United States Patent
Bathe

(12) 
(10) Patent No.: US 6,536,859 B1
(45) Date of Patent: Mar. 25, 2003

(54) CLIMATIC CABINET

(75) Inventor: Wolfgang Bathe, Jena (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 09/631,519

(22) Filed: Aug. 3, 2000

(30) Foreign Application Priority Data

Aug. 3, 1999 (DE) ......................................... 199 36 572

(51) Int. Cl.⁷ ............................................. A47B 88/18
(52) U.S. Cl. ....................... 312/305; 211/163; 221/277; 414/416.04
(58) Field of Search .............................. 211/41.12, 163, 211/1.53; 221/277, 268, 62, 224; 414/416.04, 416.09; 108/103, 139; 312/305, 125, 135, 249.2

(56) References Cited

U.S. PATENT DOCUMENTS

| | | | |
|---|---|---|---|
| 3,653,541 A | * 4/1972 | Crum | 221/268 X |
| 4,720,463 A | 1/1988 | Farber et al. | |
| 4,724,774 A | * 2/1988 | Wiedemar et al. | 312/305 X |
| 5,148,944 A | * 9/1992 | Kaufman et al. | 221/268 X |
| 5,498,543 A | 3/1996 | Berndt | |
| 5,735,587 A | * 4/1998 | Malin et al. | 312/305 |
| 5,988,431 A | * 11/1999 | Roe | 221/277 X |
| 6,129,428 A | * 10/2000 | Helwig et al. | 312/305 X |
| 6,142,336 A | * 11/2000 | Freudelsperger | 221/268 X |

FOREIGN PATENT DOCUMENTS

| | | |
|---|---|---|
| DE | 21 30 705 | 12/1971 |
| DE | 43 00231 | 12/1993 |
| DE | 197 50 912 | 5/1999 |
| EP | 07 25 133 | 8/1996 |
| JP | 4-234973 | 8/1992 |
| JP | 0707551 | 3/1995 |
| JP | 09 121837 | 5/1997 |
| WO | WO 98 59 033 | 12/2000 |

OTHER PUBLICATIONS

*English Abstract of DE 43 00231.
*English Abstract of DE 21 30 705.
*English Abstract of DE 197 50 912.
*English Abstract of WO 98 59 033.
*English Abstract of EP 07 25 133.
*English Abstract of JP 4–234973.
*English Abstract of JP 09 121837.
*English Abstract of JP 0707551.

* cited by examiner

Primary Examiner—John G. Weiss
Assistant Examiner—Michael J Fisher
(74) Attorney, Agent, or Firm—Reed Smith LLP

(57) ABSTRACT

A climatic cabinet for receiving objects, preferably microtiter plates, which contains a preferably rotatable object receptacle in the interior. The object receptacle is vertically adjustable for changing its position relative to an input and output door. The object receptacle is adjustable in a raised position with respect to its position relative to the input and output door.

4 Claims, 4 Drawing Sheets

CLIMATIC CABINET

BACKGROUND OF THE INVENTION a) Field of the Invention

UHTS is the abbreviation for "Ultra High Throughput Screening" and refers to a process in the pharmaceutical industry for screening specimens at a very high throughput (more than 100,000 specimens per day). A UHTS system is one comprising various components (such as incubators, pipetters, readers) and a transport system by which microtiter plates (MTPs) are transported between the various components. Different process steps are carried out in the components.

A UHTS system is usually divided into various work stations dedicated to different tasks and comprising components suited to these tasks.

In order to configure a work station comprising different components, it is necessary to define exactly the space to be occupied by each component. Further, it is desirable to keep the surface area requirement of a work station as small as possible. For this reason, only a relatively small surface area is available for each component.

The "small incubator" described in the following is intended to be used in a UHTS system. Its object is the interim storage of small to medium-sized quantities of microtiter plates under well-defined climatic conditions. Buffer stations of this kind are frequently required when a work station contains components with a low MTP throughput or when repeated measurements must be carried out on a microtiter plate at determined time intervals.

b) Description of the Related Art

Incubators are already known from EP 281547, EP 293782, EP 165172, DE 29613557. However, these devices cannot be integrated in a work station because they take up too large a surface area. The arrangement of a handling system in the interior of the climatic chamber, known from EP 165172, is technically complicated.

OBJECT AND SUMMARY OF THE INVENTION

The object of the invention is to provide a small automatic incubator which is adapted to the space circumstances of a work station, i.e., in particular, it has a small base area. This small base area is achieved through the special MTP storage magazine and the MTP output unit.

In accordance with the invention, a climatic cabinet for receiving objects, preferably microtiter plates, contains a preferably rotatable object receptacle in the interior. The object receptacle is vertically adjustable for changing its position relative to the input and output door.

BRIEF DESCRIPTION DRAWINGS

In the drawings

DESCRIPTION OF THE PREFERRED EMBODIMENTS

Figure 1:
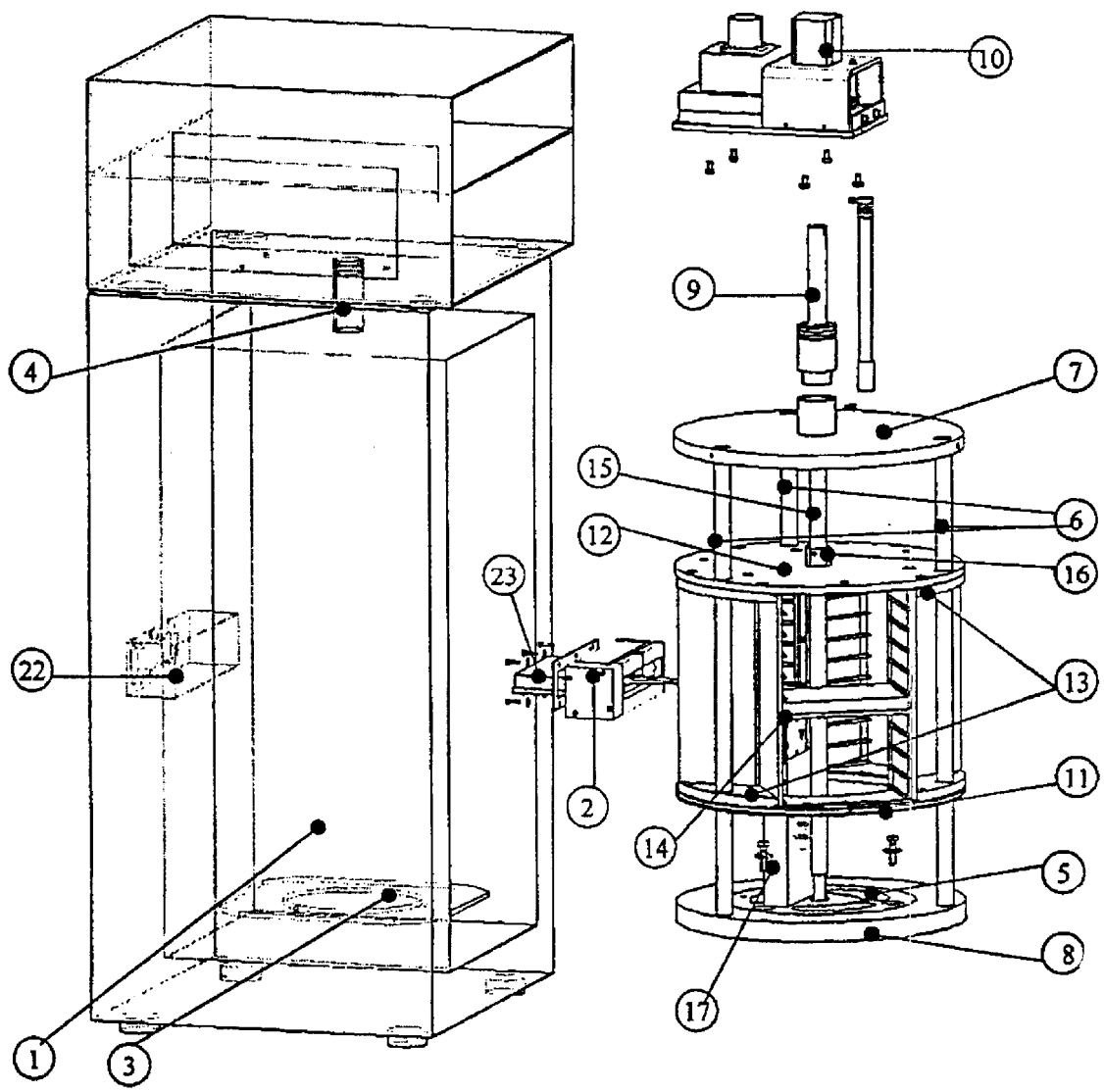
FIG. 1 illustrates a small automatic incubator in an exploded view.

FIG. 1 shows the small automatic incubator in an exploded view. At the left in the drawing is the climatic cabinet 1, at the right is the mechanism which is located in the climatic cabinet 1 during operation. This mechanism is an automated storage magazine which has available space for 30 microtiter plates, for example. This storage magazine can automatically output any MTP to the surrounding system. The input of an MTP, on the other hand, is effected from the surrounding system. In this case, the storage magazine is prepared for an input beforehand. The exact description of the sequences of functions will be given in the following.

The climatic cabinet (1) advantageously contains all of the elements necessary for the climate control (regulation of temperature, relative proportion of carbon dioxide and generation of a relative humidity of 90%) of the interior space. In particular, these elements, which correspond to the prior art and are not shown here, are a housing with insulation and air jacket, sensors, heating elements, $CO_2$ valve and evaporation pan, as well as a large door on the right-hand side of the incubator.

Further, the climatic cabinet contains an automatically locking door lock (2) (automatic door shown in FIG. 1 between the MTP magazine and the climatic cabinet) on the left-hand side wall which is inserted into an opening provided for this purpose, fastening means 3 for the internal mechanism to be described in the following, and a through-guide 4 for the drive shaft/hollow shaft (9) of the storage magazine.

Figure 4:
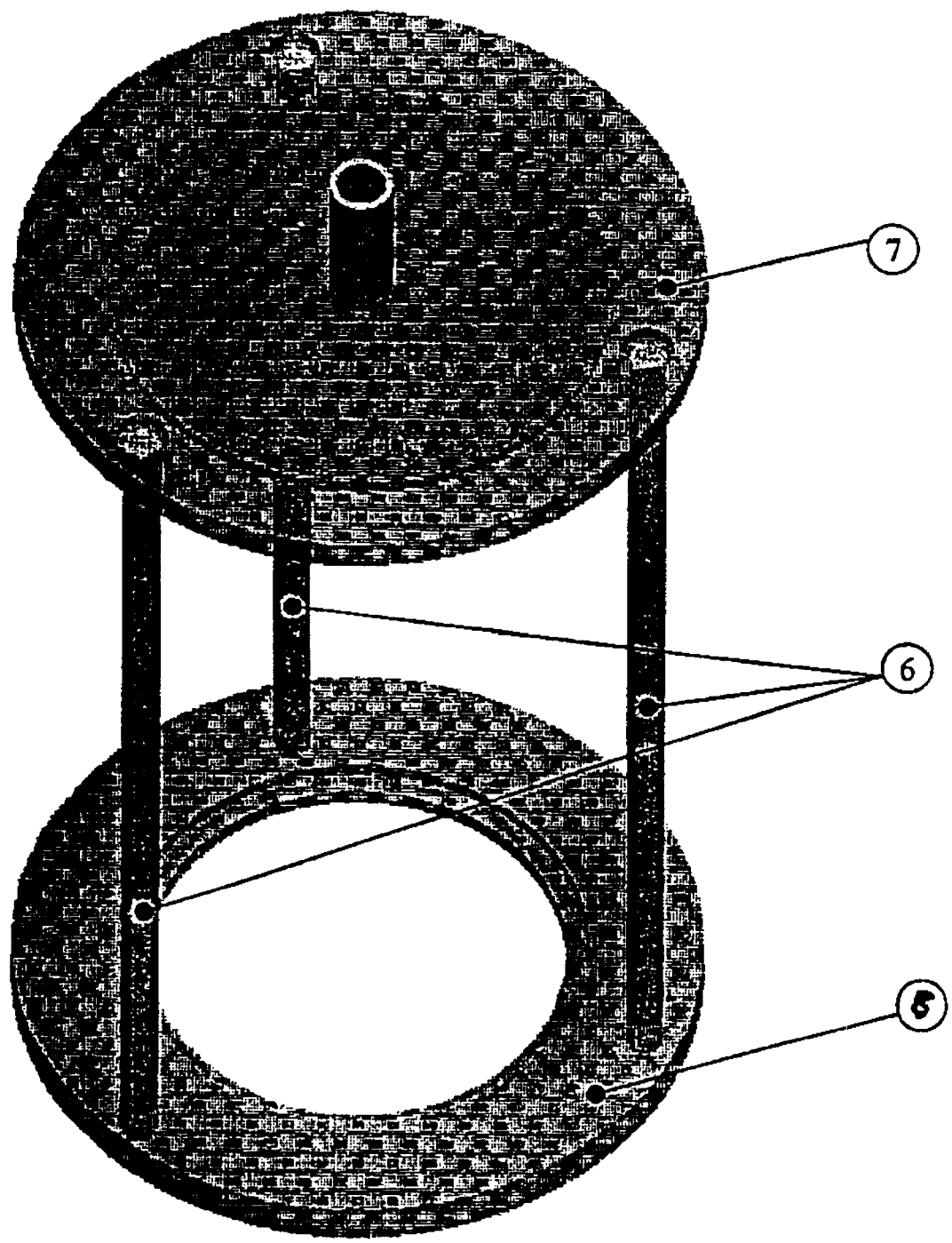
FIG. 4 illustrates the storage magazine.

The storage magazine is formed of a carousel which is shown separately in FIG. 4 and which comprises a frame construction with a ring (5) at bottom, three guide rods (6) and an upper closing plate (7). The frame construction is mounted so as to be rotatable. For this purpose, the ring has a thrust bearing or counter-bearing which is formed of a round, stationary platform (8) which is enclosed by the ring 5. A hollow shaft (9) which is connected with the carousel and which is guided through the through-guide 4 in the climatic cabinet (4) is mounted at the closing plate 7. The upper end of the hollow shaft 9 is coupled to a drive unit (10) (e.g., a stepper motor with gear unit). The drive unit 10 is constructed in such a way that it permits an exact positioning of the adjusting angle of the carousel.

Figure 5:
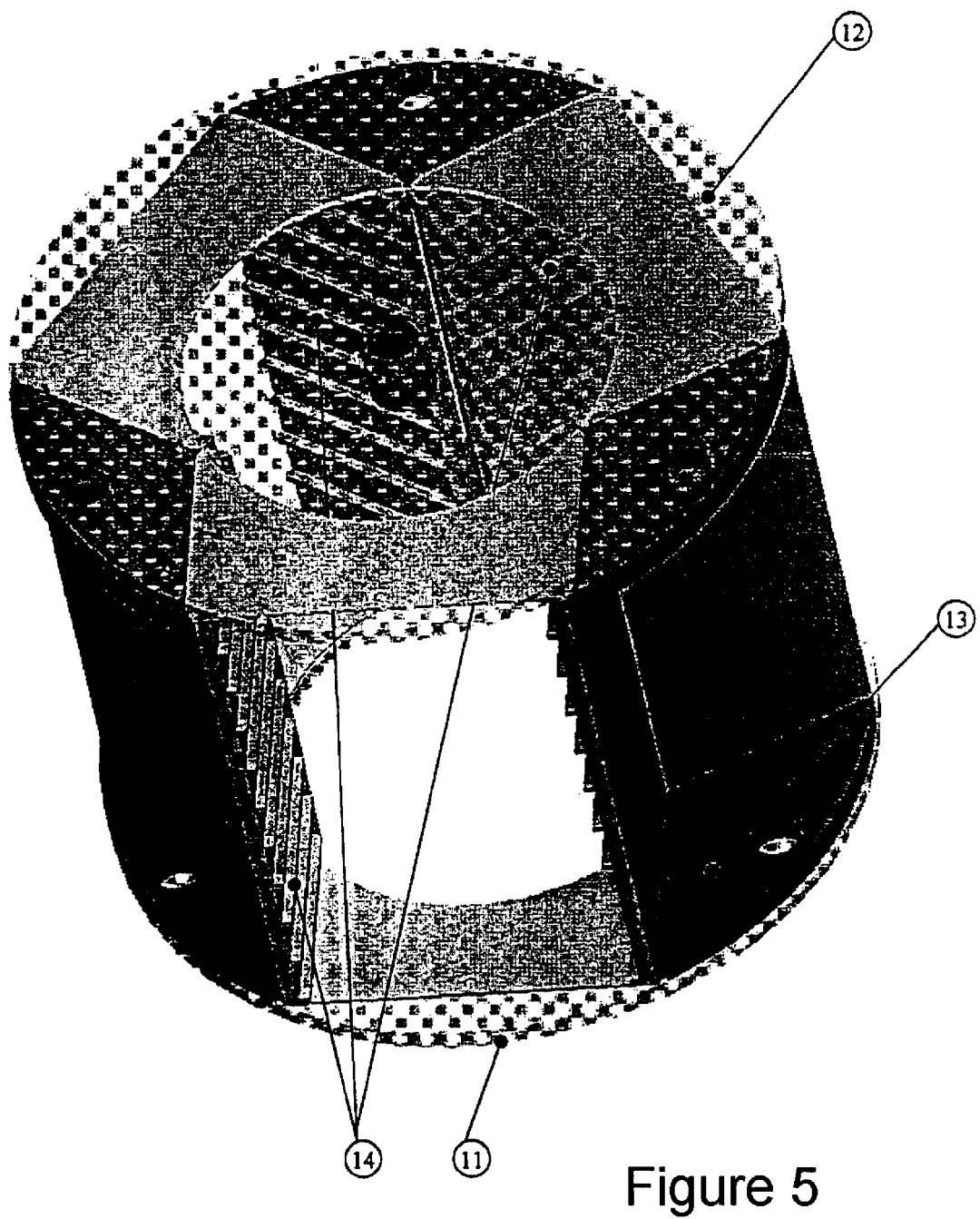
FIG. 5 illustrates a magazine receptacle.

The carousel contains a magazine receptacle, shown separately in FIG. 5, for three microtiter plate magazines. This magazine receptacle is formed of a bottom ring (11), a cover plate (12) and three connection elements (13). An MTP magazine (14) is inserted in each of the three intermediate spaces and is held therein by a retainer. The magazine receptacle is guided vertically by the guide rods (6). The vertical adjustment of the magazine receptacle is achieved by means of rotation of a centrally arranged spindle (15). For this purpose, the magazine receptacle has a nut (16) which is fastened to the cover plate and which is guided by the spindle 15. The spindle 15 is guided through the hollow shaft (9). It is driven at the upper end by another drive unit which is likewise located in the drive unit 10. This drive unit allows the vertical positioning of the magazine receptacle.

Figure 2:
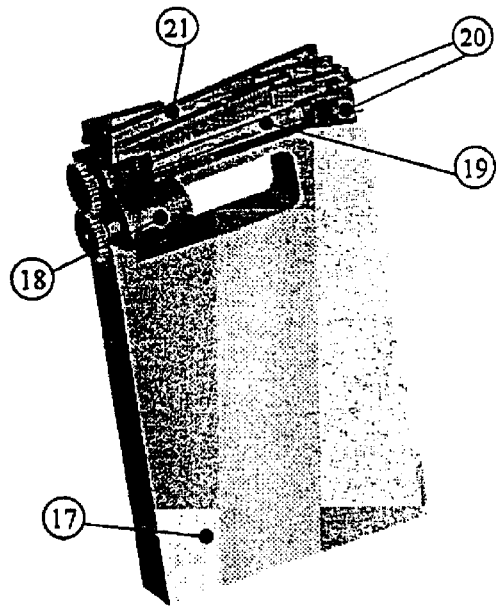
FIG. 2 illustrates the push-out device on the push-out block.

The MTPs are transferred to the surrounding system by a push-out device shown in FIG. 2. Because of its design (double scissors with spindle drive), the push-out device can be built so compactly that it fits on a push-out block (17) which stands on the inner stationary platform 8. The push-out block is just high enough that the height of the push-out device conforms to the height of the automatic door (2).

The push-out device pushes an MTP outward out of the storage magazine in radial direction via guide rails through the open automatic door to the surrounding system. When the MTP magazines rotate, they are moved up by the vertical positioning means until the push-out device is located below the MTP receptacles.

FIG. 2 shows the push-out device on the push-out block (17) which stands on the inner stationary platform 8. The push-out block is just high enough so that its height conforms to the height of the automatic door 2. The drive unit of the push-out device (18) is formed of a coded motor (e.g., a stepper motor) which drives a spindle (19). This spindle has two threads, a right-handed thread and a left-handed thread. Nuts (20) run on both thread positions. These nuts move toward one another during rotation in a corresponding rotating direction and away from each other in the opposite rotating direction. An arm of a double scissor (21) is coupled to each of the nuts. When the nuts are moved apart as shown in FIG. 2 the scissors are folded together. When the nuts move toward one another, the scissors unfold in a direction vertical to the spindle. The end points of the scissors push the MTPs in the desired radial direction.

An outer pusher, not shown, which pushes the MTPs into the incubator is provided for feeding the MTPs into the incubator.

The automatic door (2) is constructed in such a way that it can be inserted tightly into the provided opening of the climatic cabinet (22).

Description of the Function Sequences

The automatic incubator allows the system to access any microtiter plate stored at any location in the magazine. For this purpose, the corresponding magazine space is moved into the transfer position. After this, the magazine space can be loaded or unloaded.

The positioning of the magazine comprises a maximum of three partial steps. These partial steps are shown in FIG. 3.

Figure 3:
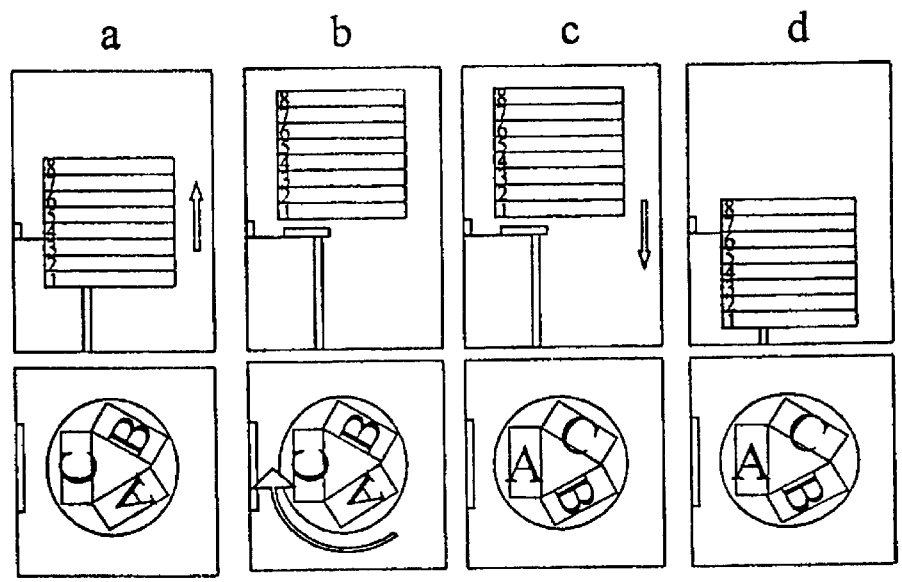
FIG. 3 shows the automatic incubator schematically in a front view and in a plan view.

FIG. 3 shows the automatic incubator schematically in a front view (top) and in a plan view (bottom). The automatic door and the push-out device are likewise indicated since they determine the transfer position.

The carousel has three magazines, each magazine comprising eight tiers for MTPs. In FIG. 3a, the magazine space 4 of the magazine shaft C is in the transfer position. For example, magazine space A7 is moved into the transfer position. This is carried out in three partial steps: the carousel is moved fully upward so that the push-out device no longer penetrates into the carousel. The state which is reached is shown in 3b.

In the topmost position of the carousel, it can be rotated. In the lower positions, this is not possible because the push-out device blocks the way. Position 3c is reached by rotating the carousel. The carousel is now lowered again until the plane 7 is located at transfer height. Magazine space A7 is now in the transfer position as is indicated by 3d.

The input and output of the MTPs comprises a total of four partial steps. First, the input of an MTP is effected as follows: The storage magazine is positioned. A free space is moved into the transfer position. The automatic door is opened. The MTP is pushed in by the surrounding system. The automatic door is closed. This concludes the process. The output is effected in an analogous manner: The storage magazine is positioned. The storage space with the MTPs to be pushed out is moved into the transfer position. The automatic door is opened. The MTPs are pushed out by the push-out device. The automatic door is closed.

While the foregoing description and drawings represent the preferred embodiments of the present invention, it will be obvious to one skilled in the art that various changes and modifications may be made therein without departing from the true spirit and scope of the present invention.

What is claimed is:

1. A climatic cabinet for receiving microtiter plates, comprising:

a climatic cabinet capable of controlling the climate in said climatic cabinet;

an ultra high throughput screening rotatable object receptacle contained in the interior of the climatic cabinet for holding microtiter plates;

said ultra high throughput screening object receptacle being vertically adjustable for changing its position relative to an input and output door of the receptacle; and said input and output door being automatically locked.

2. The climatic cabinet according to claim 1, wherein the object receptacle is adjustable in a raised position with respect to its position relative to the input and output door.

3. The climatic cabinet according to claim 1, wherein the rotatable object receptacle includes a plurality of object storages.

4. The climatic cabinet according to claim 1, wherein a stationary push-out device is arranged for directing the objects outwardly, the object receptacle being positioned relative thereto.

* * * * *